(12) United States Patent
Tseng et al.

(10) Patent No.: US 10,479,811 B1
(45) Date of Patent: Nov. 19, 2019

(54) PROCESS FOR PREPARING CYCLOPHOSPHAMIDE, INTERMEDIATES, AND MONOHYDRATE THEREOF

(71) Applicant: PHARMACORE BIOTECH CO., LTD., Tainan (TW)

(72) Inventors: Wei-Hong Tseng, Tainan (TW); Vallapa Soong, Tainan (TW); Ko Hua Yu, Tainan (TW); Hsing Yu Chang, Tainan (TW); Chia-Yu Lin, Tainan (TW)

(73) Assignee: PHARMACORE BIOTECH CO., LTD., Tainan (TW)

( * ) Notice: Subject to any disclaimer, the term of this patent is extended or adjusted under 35 U.S.C. 154(b) by 0 days.

(21) Appl. No.: 16/210,066

(22) Filed: Dec. 5, 2018

(51) Int. Cl.
    *C07F 9/6584* (2006.01)
    *A61P 37/06* (2006.01)
    *A61P 35/00* (2006.01)

(52) U.S. Cl.
    CPC .......... *C07F 9/65846* (2013.01); *A61P 35/00* (2018.01); *A61P 37/06* (2018.01); *C07B 2200/13* (2013.01)

(58) Field of Classification Search
    CPC .................................. C07F 9/65846
    See application file for complete search history.

(56) References Cited

PUBLICATIONS

Chiu et al. "Synthesis, hydrolytic reactivity, and anticancer evaluation of N- and 0-triorganosilylated compounds as new types of potential prodrugs" Journal of Pharmaceutical Sciences, 1982, vol. 71, No. 5, pp. 542-551.*

* cited by examiner

*Primary Examiner* — Joseph R Kosack
(74) *Attorney, Agent, or Firm* — WPAT, PC (57) ABSTRACT

The present disclosure provides a process for preparing cyclophosphamide, intermediate, and the monohydrate thereof.

12 Claims, 6 Drawing Sheets

PROCESS FOR PREPARING CYCLOPHOSPHAMIDE, INTERMEDIATES, AND MONOHYDRATE THEREOF

BACKGROUND OF THE INVENTION

1. Field of the Invention

The present invention relates to a process for preparing cyclophosphamide. In particular, the present invention relates to a process for preparing cyclophosphamide, intermediates, and the monohydrate thereof.

2. The Prior Art

Cyclophosphamide (CPA), also known as cytophosphane, is a medication used as chemotherapy and to suppress the immune system. As chemotherapy it is used to treat lymphoma, multiple myeloma, leukemia, ovarian cancer, breast cancer, small cell lung cancer, neuroblastoma, and sarcoma. As an immune suppressor it is used in nephrotic syndrome, granulomatosis with polyangiitis, and following organ transplant. It is taken by mouth or injection into a vein. The chemical name of cyclophosphamide is NN-bis(2-chloroethyl)-1,3,2-oxazaphosphinan-2-amine 2-oxide and represented as follows:

Currently, there are various processes for the preparation and synthesis of cyclophosphamide. However, conventional processes have the disadvantages of low product yield, low purity, time-consuming, and incapability of large-scale production.

Thus, there is a need to develop an industrially feasible, economically viable, commercially up-scalable process which may be safer for handling, less time consuming and which provides the product with improved yield and pharmacopoeial purity.

SUMMARY OF THE INVENTION

A primary objective of the present invention is to provide a process for preparing cyclophosphamide monohydrate, comprising the steps of: (a) providing bis (2-chloroethyl) amine hydrochloride; (b) converting bis (2-chloroethyl) amine hydrochloride into cyclophosphamide monohydrate represented as formula I, and wherein the converting comprises the step of reacting bis (2-chloroethyl) amine hydrochloride with phosphorus oxychloride in the presence of a base in toluene at a temperature ranging from 20° C. to 60° C. to form bis-(2-chloroethyl)-phosphoramidic dichloride represented as formula II:

wherein the bis-(2-chloroethyl)-phosphoramidic dichloride represented as formula II is converted into the cyclophosphamide represented by reacting with 3-amino-1-propanol in the presence of the base in a solvent and purifying and isolating to yield a crystalline of cyclophosphamide monohydrate represented as formula I.

According to an embodiment of the present invention, the base in solid, liquid or aqueous form is selected from the group consisting of aromatic amine, aliphatic amine and a mixture thereof.

According to an embodiment of the present invention, a mole ratio of the base to the bis-(2-chloroethyl)-phosphoramidic dichloride represented as formula II is 1.0 to 1.5.

According to an embodiment of the present invention, the solvent is selected from the group consisting of halogenated solvent, ester and aromatic hydrocarbon.

According to an embodiment of the present invention, the bis-(2-chloroethyl)-phosphoramidic dichloride represented as formula II has a purity level greater than 98% by high performance liquid chromatography.

According to an embodiment of the present invention, the cyclophosphamide monohydrate represented as formula I has a purity of 99% or higher.

According to an embodiment of the present invention, the process further comprises crystallizing a new crystalline form A of the bis-(2-chloroethyl)-phosphoramidic dichloride represented as formula II by using a solution comprising toluene and n-heptane.

According to an embodiment of the present invention, the crystalline form A of the bis-(2-chloroethyl)-phosphoramidic dichloride represented as formula II is characterized by X-ray powder diffraction pattern comprising the characteristic 2θ° peaks of 13.8, 14.4, 15.4, 19.9, 23.6, 26.9, 29.0, 29.65, 31.0 and 31.9±0.2°, wherein peaks at 30.9 and 31.1±0.2° are un-split and 100% intensity peak is present at 23.6±0.2°, infrared absorption spectrum comprising the characteristic peaks approximately at 2959.5 cm$^{-1}$, 1459.3 cm$^{-1}$, 1263.3 cm$^{-1}$, 1226.3 cm$^{-1}$ and 980.3 cm$^{-1}$, and differential scanning calorimetry (DSC) exhibits melting points ranging from 56-58° C.

Figure 1:
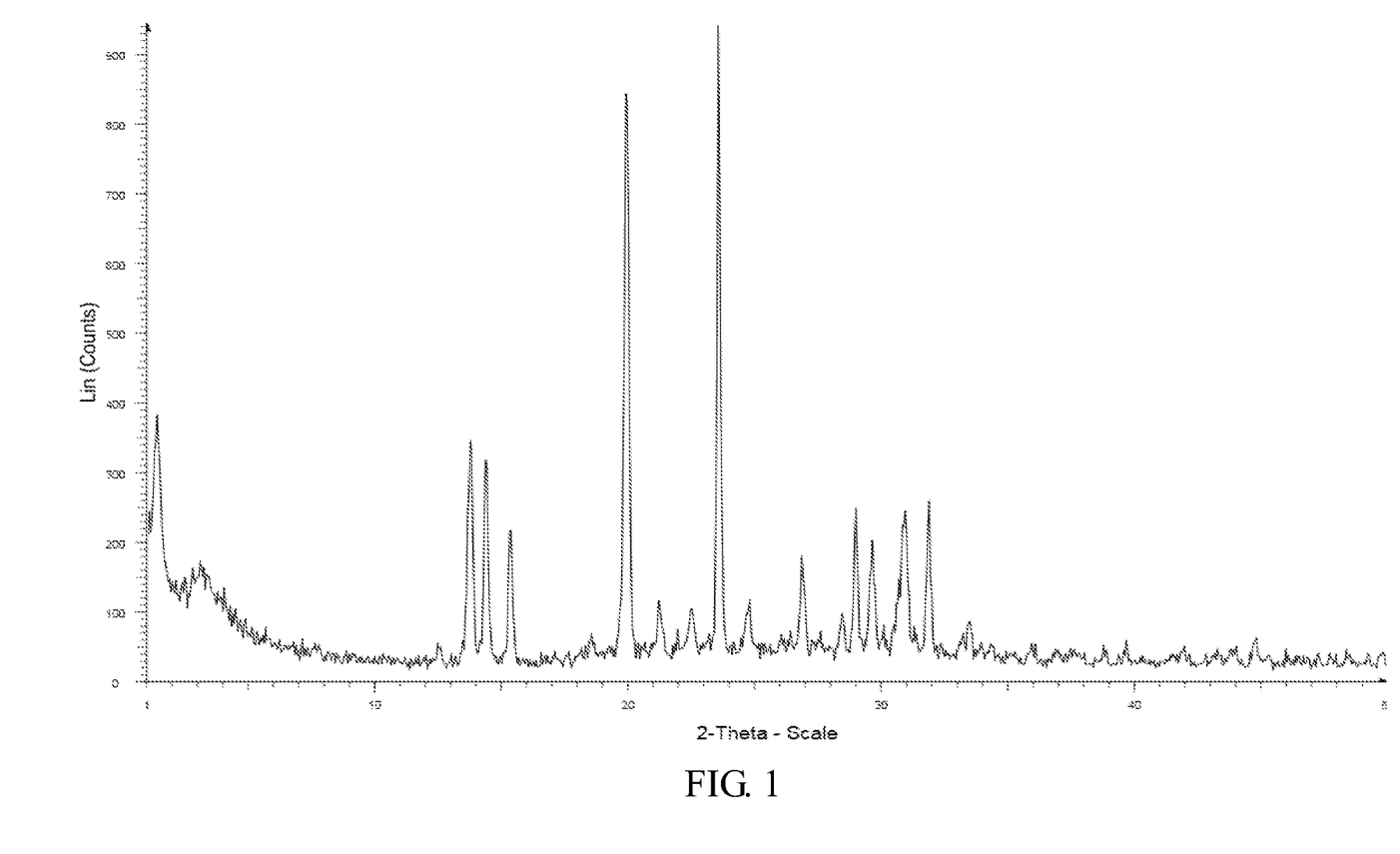
FIG. 1 shows the X-ray powder diffraction pattern of the crystalline form A of the bis-(2-chloroethyl)-phosphoramidic dichloride represented as formula II.
Figure 2:
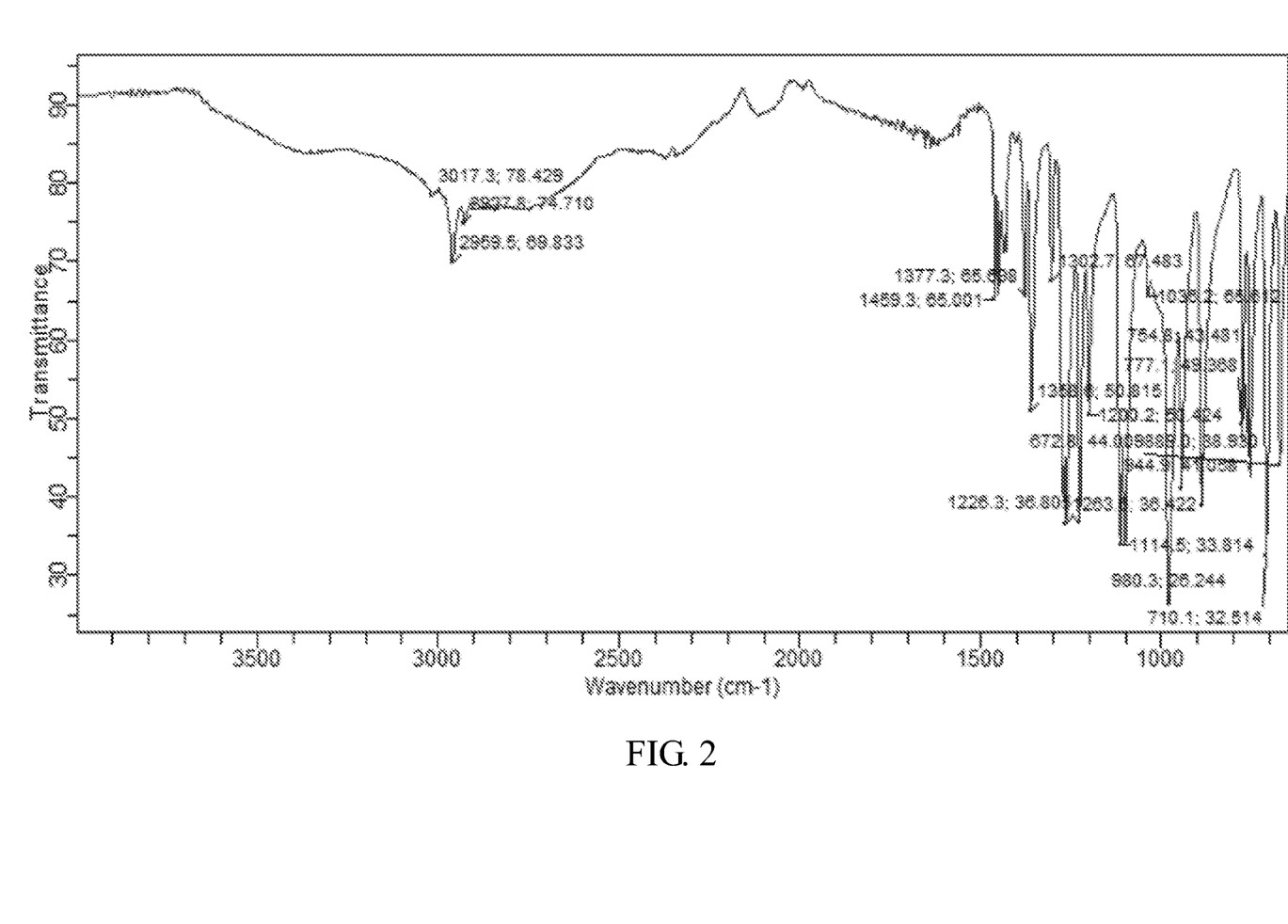
FIG. 2 shows infrared absorption spectrum of the crystalline form A of the bis-(2-chloroethyl)-phosphoramidic dichloride represented as formula II.
Figure 3:
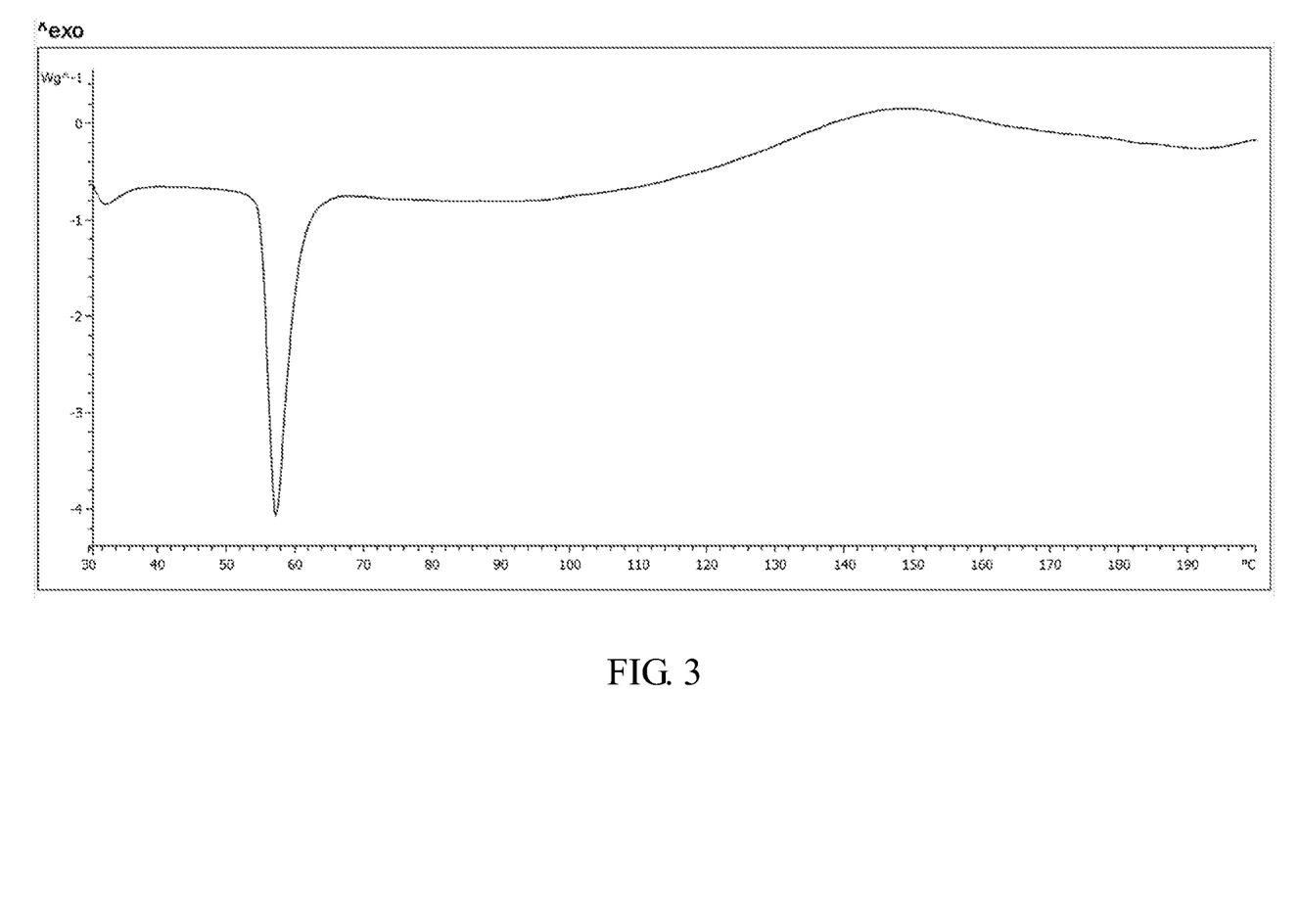
FIG. 3 shows differential scanning calorimetry of the crystalline form A of the bis-(2-chloroethyl)-phosphoramidic dichloride represented as formula II.

According to an embodiment of the present invention, the X-ray powder diffraction pattern of a new crystalline form A of the bis-(2-chloroethyl)-phosphoramidic dichloride represented as formula II is substantially in accordance with FIG. 1, the infrared absorption spectrum of the crystalline form A of the bis-(2-chloroethyl)-phosphoramidic dichloride represented as formula II is substantially in accordance with FIG. 2, and the differential scanning calorimetry of the bis-(2-chloroethyl)-phosphoramidic dichloride represented as formula II is substantially in accordance with FIG. 3.

Another objective of the present invention is to provide a process for preparing a sterile of the cyclophosphamide monohydrate represented as formula I, comprising dissolving the abovementioned crystalline of cyclophosphamide monohydrate represented as formula I in a crude solution comprising dichloromethane, tert-butyl methyl ether, and water.

According to an embodiment of the present invention, the sterile of the cyclophosphamide monohydrate represented as formula I is characterized by X-ray powder diffraction pattern comprising the characteristic 2θ° peaks of 7.0, 14.0, 14.8, 17.8, 22.0, 23.8, 26.8, 28.3 and 30.1±0.2°, wherein peaks at 26.8 and 26.9±0.2° are un-split and 100% intensity peak is present at 22.0±0.2°, infrared absorption spectrum comprising the characteristic peaks approximately at 3432.9 cm$^{-1}$, 3185.0 cm$^{-1}$, 1453.7 cm$^{-1}$, 1217.0 cm$^{-1}$, 1179.7 cm$^{-1}$, 1047.4 cm$^{-1}$ and 950.5 cm$^{-1}$, and differential scanning calorimetry (DSC) exhibits melting points ranging from 51-53° C.

Figure 4:
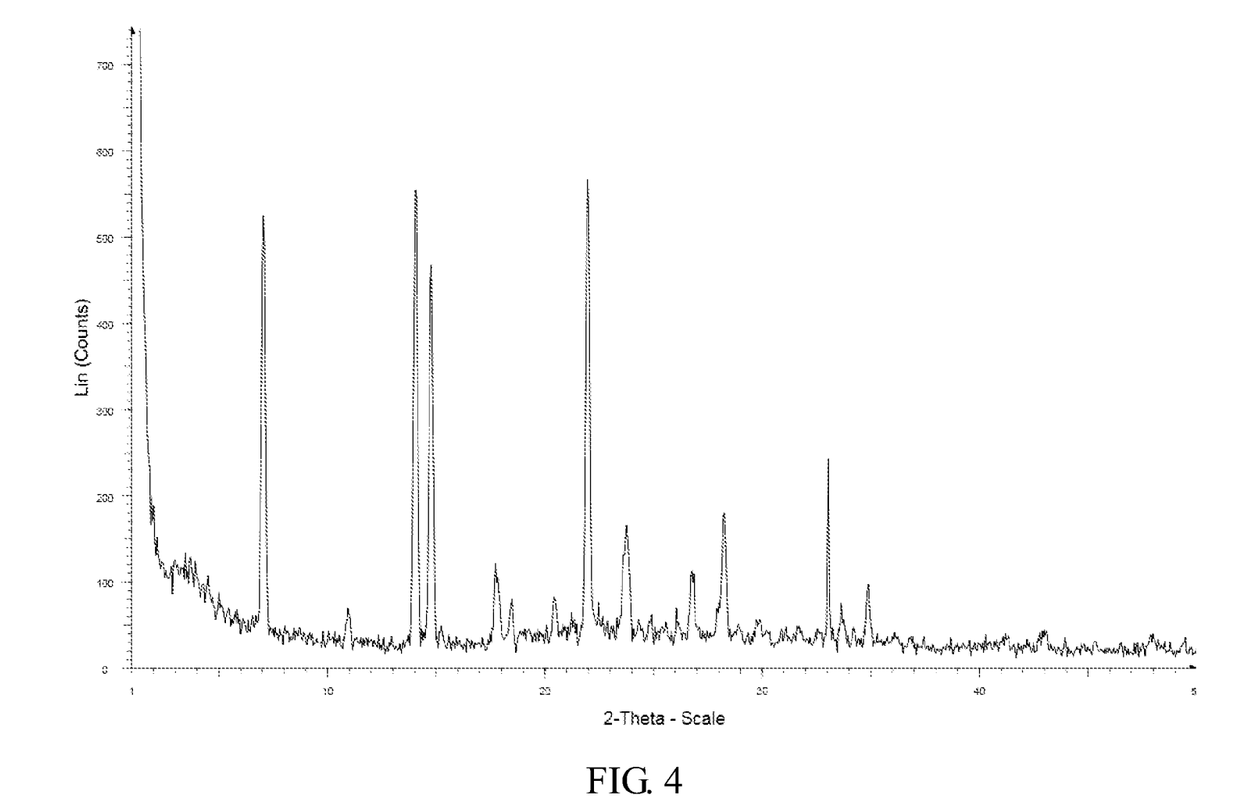
FIG. 4 shows the X-ray powder diffraction pattern of the monohydrate of the cyclophosphamide represented as formula I.
Figure 5:
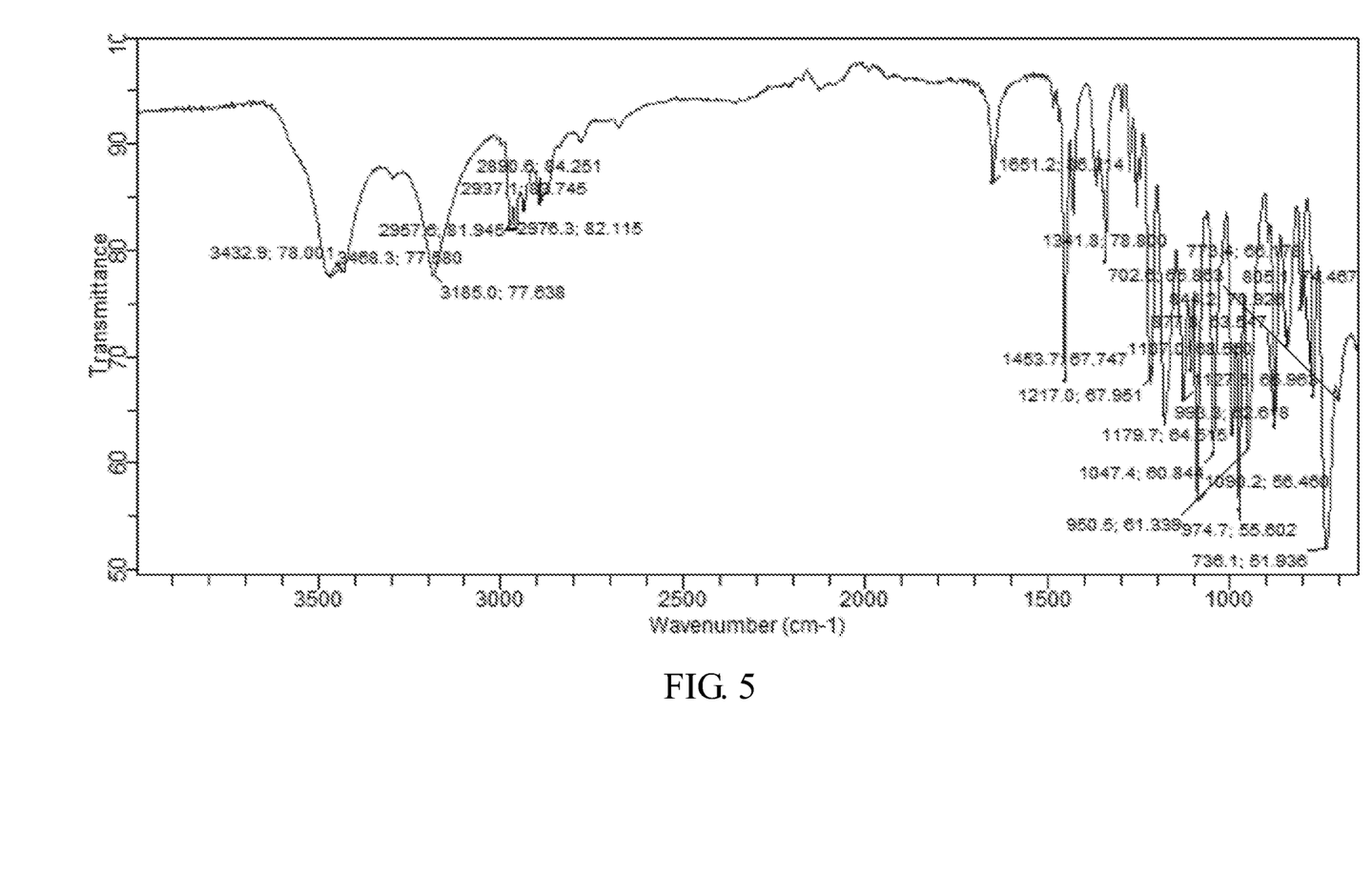
FIG. 5 shows infrared absorption spectrum of the monohydrate of the cyclophosphamide represented as formula I.
Figure 6:
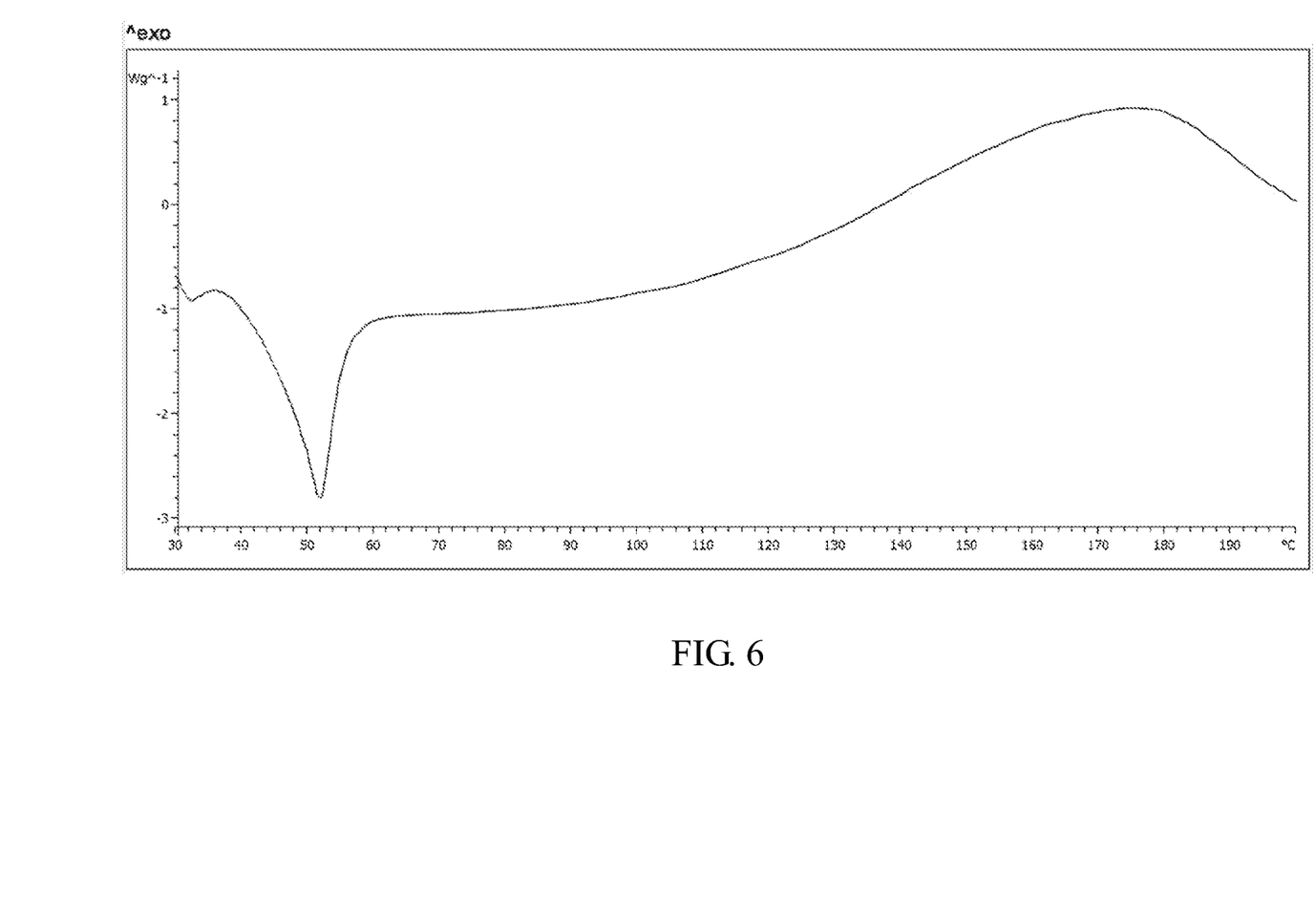
FIG. 6 shows differential scanning calorimetry of the monohydrate of the cyclophosphamide represented as formula I.

According to an embodiment of the present invention, the X-ray powder diffraction pattern of the sterile of the cyclophosphamide monohydrate represented as formula I is substantially in accordance with FIG. 4, the infrared absorption spectrum of the sterile of the cyclophosphamide monohydrate represented as formula I is substantially in accordance with FIG. 5 and the differential scanning calorimetry of the sterile of the cyclophosphamide monohydrate represented as formula I is substantially in accordance with FIG. 6

Accordingly, the advantageous effect of the present invention is to provide an industrially feasible, economically viable, commercially up-scalable process which may be safer for handling, less time consuming and which provides the product with improved yield and pharmacopoeial purity.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

The purity of the solid forms provided herein may be determined by standard analytical methods, such as thin layer chromatography (TLC), gel electrophoresis, gas chromatography, high performance liquid chromatography (HPLC), and mass spectrometry (MS).

It should be understood that the numerical values of the peaks of an X-ray powder diffraction pattern may vary slightly from one machine to another or from one sample to another, and so the values quoted are not to be construed as absolute, but with an allowable variability, such as ±0.2 degree (see United State Pharmacopoeia, page 2228 (2003)).

The complete synthetic route of cyclophosphamide monohydrate is shown in the following scheme:

Example 1 Preparation of Cyclophosphamide Monohydrate and its Intermediates

First, bis (2-chloroethyl) amine hydrochloride ($C_4H_{10}Cl_3N$) represented as follows was reacted with 1.3 equivalent of phosphorus oxychloride ($POCl_3$) in the presence of a base (i.e., triethanolamine, TEA) in toluene at a temperature ranging from 20° C. to 60° C.:

C₄H₁₀Cl₃N
MW: 178.48

In particular, the base in solid, liquid or aqueous form is selected from the group consisting of aliphatic amine, aromatic amine and a mixture thereof.

Thereafter, an intermediate of the cyclophosphamide was isolated, wherein the intermediate is bis-(2-chloroethyl)-phosphoramidic dichloride ($C_4H_8Cl_4NOP$) represented as formula II:

$C_4H_8Cl_4NOP$
MW: 258.89

In particular, a mole ratio of the base to the bis-(2-chloroethyl)-phosphoramidic dichloride represented as formula II is 1.0 to 1.5.

Subsequently, the bis-(2-chloroethyl)-phosphoramidic dichloride represented as formula II was reacted with 1.05 equivalent of 3-amino-1-propanol represented as follows in the presence of the base (i.e., TEA) in a solvent (i.e., dichloromethane, $CH_2Cl_2$) to obtain the cyclophosphamide monohydrate represented as formula I:

$C_7H_{17}Cl_2N_2O_3P$
MW: 279.10

In particular, the solvent is selected from the group consisting of halogenated solvent, ester and aromatic hydrocarbon.

In particular, the obtained bis-(2-chloroethyl)-phosphoramidic dichloride represented as formula II as a pale yellow powder has a purity level greater than 98% by high performance liquid chromatography. The cyclophosphamide monohydrate represented as formula I has a purity of 99% or higher.

The crystalline form A of the bis-(2-chloroethyl)-phosphoramidic dichloride represented as formula II was prepared by dissolving the bis-(2-chloroethyl)-phosphoramidic dichloride represented as formula II in a solution comprising about 2 volume of toluene and 5 volume n-heptane based on the weight of starting material.

The X-ray powder diffraction pattern of the new crystalline form A of the bis-(2-chloroethyl)-phosphoramidic dichloride represented as formula II is shown in FIG. 1, infrared absorption spectrum of the new crystalline form A of the bis-(2-chloroethyl)-phosphoramidic dichloride represented as formula II is shown in FIG. 2, and differential scanning calorimetry of the new crystalline form A of the bis-(2-chloroethyl)-phosphoramidic dichloride represented as formula II is shown in FIG. 3. As shown in FIG. 1, the crystalline form A of the bis-(2-chloroethyl)-phosphoramidic dichloride represented as formula II is characterized by X-ray powder diffraction pattern comprising the characteristic 2θ° peaks of 13.8, 14.4, 15.4, 19.9, 23.6, 26.9, 29.0, 29.65, 31.0 and 31.9±0.2°, wherein peaks at 30.9 and 31.1±0.2° are un-split and 100% intensity peak is present at 23.6±0.2°. As shown in FIG. 2, the new crystalline form A of the bis-(2-chloroethyl)-phosphoramidic dichloride represented as formula II is characterized by infrared absorption spectrum comprising the characteristic peaks approximately at 2959.5 cm$^{-1}$, 1459.3 cm$^{-1}$, 1263.3 cm$^{-1}$, 1226.3 cm$^{-1}$ and 980.3 cm$^{-1}$. Also, it has melting points of about 56-58° C. as measured by differential scanning calorimetry (DSC) as shown in FIG. 3.

Example 2 Preparation of Monohydrate of Cyclophosphamide

The monohydrate of the cyclophosphamide was prepared by dissolving the cyclophosphamide obtained in Example 1 in a crude solution comprising about 2 volume of dichloromethane, 1.5 volume of tert-butyl methyl ether, and 0.5 volume water based on the weight of formula II. The product obtained in this example is distributed in aseptic conditions, to sterilized glass and tightly sealed.

The crystalline cyclophosphamide monohydrate shows water content in the range of 6.2 to 6.8% by Karl Fischer water content determination method.

The X-ray powder diffraction pattern of the monohydrate of the cyclophosphamide is shown in FIG. 4, infrared absorption spectrum of the monohydrate of the cyclophosphamide is shown in FIG. 5 and differential scanning calorimetry of the monohydrate of the cyclophosphamide is shown in FIG. 6. As shown in FIG. 4, the monohydrate of the cyclophosphamide is characterized by X-ray powder diffraction pattern comprising the characteristic 2θ° peaks of 7.0, 14.0, 14.8, 17.8, 22.0, 23.8, 26.8, 28.3 and 30.1±0.2°, wherein peaks at 26.8 and 26.9±0.2° are un-split and 100% intensity peak is present at 22.0±0.2°. As shown in FIG. 5, the monohydrate of the cyclophosphamide is characterized by infrared absorption spectrum comprising the characteristic peaks approximately at 3432.9 cm$^{-1}$, 3185.0 cm$^{-1}$, 1453.7 cm$^{-1}$, 1217.0 cm$^{-1}$, 1179.7 cm$^{-1}$, 1047.4 cm$^{-1}$ and 950.5 cm$^{-1}$. Also, it has melting points of about 51-53° C. as measured by differential scanning calorimetry (DSC) as shown in FIG. 6.

In summary, the present invention provides an industrially feasible, economically viable, commercially up-scalable process which may be safer for handling, less time consuming and which provides the product with improved yield and pharmacopoeial purity.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A process for preparing cyclophosphamide monohydrate, comprising the steps of:
   (a) providing bis (2-chloroethyl) amine hydrochloride;
   (b) converting bis (2-chloroethyl) amine hydrochloride into cyclophosphamide monohydrate represented as formula I, and

I wherein the converting comprises the step of reacting bis (2-chloroethyl) amine hydrochloride with phosphorus oxychloride in the presence of a base in toluene at a temperature ranging from 20° C. to 60° C. to form bis-(2-chloroethyl)-phosphoramidic dichloride represented as formula II:

II wherein the bis-(2-chloroethyl)-phosphoramidic dichloride represented as formula II is converted into the cyclophosphamide represented as formula I by reacting with 3-amino-1-propanol in the presence of the base in a solvent and purifying and isolating to yield a crystalline of cyclophosphamide monohydrate represented as formula I.

2. The process according to claim 1, wherein the base in solid, liquid or aqueous form is selected from the group consisting of aliphatic amine, aromatic amine and a mixture thereof.

3. The process according to claim 1, wherein a mole ratio of the base to the bis-(2-chloroethyl)-phosphoramidic dichloride represented as formula II is 1.0 to 1.5.

4. The process according to claim 1, wherein the solvent is selected from the group consisting of halogenated solvent, ester and aromatic hydrocarbon.

5. The process according to claim 1, wherein the bis-(2-chloroethyl)-phosphoramidic dichloride represented as formula II has a purity level greater than 98% by thin layer chromatography.

6. The process according to claim 1, wherein the cyclophosphamide monohydrate represented as formula I has a purity of 99% or higher.

7. The process according to claim 1, further comprising crystallizing a crystalline form A of the bis-(2-chloroethyl)-phosphoramidic dichloride represented as formula II by using a solution comprising toluene and n-heptane.

8. The process according to claim 7, wherein the crystalline form A of the bis-(2-chloroethyl)-phosphoramidic dichloride represented as formula II is characterized by X-ray powder diffraction pattern comprising the characteristic 2θ° peaks of 13.8, 14.4, 15.4, 19.9, 23.6, 26.9, 29.0, 29.65, 31.0 and 31.9±0.2°, wherein peaks at 30.9 and 31.1±0.2° are un-split and 100% intensity peak is present at 23.6±0.2°, infrared absorption spectrum comprising the characteristic peaks approximately at 2959.5 cm$^{-1}$, 1459.3 cm$^{-1}$, 1263.3 cm$^{-1}$, 1226.3 cm$^{-1}$ and 980.3 cm$^{-1}$, and differential scanning calorimetry (DSC) exhibits melting points ranging from 56-58° C.

9. The process according to claim 8, wherein the X-ray powder diffraction pattern of the crystalline form A of the bis-(2-chloroethyl)-phosphoramidic dichloride represented as formula II is substantially in accordance with FIG. 1, and the infrared absorption spectrum of the crystalline form A of the bis-(2-chloroethyl)-phosphoramidic dichloride represented as formula II is substantially in accordance with FIG. 2.

10. A process for preparing a sterile of the cyclophosphamide monohydrate represented as formula I, comprising dissolving the crystalline of cyclophosphamide monohydrate represented as formula I according to claim 1 in a crude solution comprising dichloromethane, tert-butyl methyl ether, and water.

11. The process according to claim 10, wherein the sterile of the cyclophosphamide monohydrate represented as formula I is characterized by X-ray powder diffraction pattern comprising the characteristic 2θ° peaks of 7.0, 14.0, 14.8, 17.8, 22.0, 23.8, 26.8, 28.3 and 30.1±0.2°, wherein peaks at 26.8 and 26.9±0.2° are un-split and 100% intensity peak is present at 22.0±0.2°, and infrared absorption spectrum comprising the characteristic peaks approximately at 3432.9 cm$^{-1}$, 3185.0 cm$^{-1}$, 1453.7 cm$^{-1}$, 1217.0 cm$^{-1}$, 1179.7 cm$^{-1}$, 1047.4 cm$^{-1}$ and 950.5 cm$^{-1}$, and differential scanning calorimetry (DSC) exhibits melting points ranging from 51-53° C.

12. The process according to claim 11, wherein the X-ray powder diffraction pattern of the sterile of the cyclophosphamide monohydrate represented as formula I is substantially in accordance with FIG. 4, the infrared absorption spectrum of the sterile of the cyclophosphamide monohydrate represented as formula I is substantially in accordance with FIG. 5, and the differential scanning calorimetry (DSC) of the sterile of the cyclophosphamide monohydrate represented as formula I is substantially in accordance with FIG. 6.

* * * * *

(12) EX PARTE REEXAMINATION CERTIFICATE (11884th)
United States Patent
Tseng et al.

(10) Number: US 10,479,811 C1
(45) Certificate Issued: Jul. 26, 2021

(54) PROCESS FOR PREPARING CYCLOPHOSPHAMIDE, INTERMEDIATES, AND MONOHYDRATE THEREOF

(71) Applicant: PHARMACORE BIOTECH CO., LTD., Tainan (TW)

(72) Inventors: Wei-Hong Tseng, Tainan (TW); Vallapa Soong, Tainan (TW); Ko Hua Yu, Tainan (TW); Hsing Yu Chang, Tainan (TW); Chia-Yu Lin, Tainan (TW)

(73) Assignee: PHARMACORE BIOTECH CO., LTD., Tainan (TW)

Reexamination Request:
No. 90/014,599, Dec. 17, 2020

Reexamination Certificate for:
Patent No.: 10,479,811
Issued: Nov. 19, 2019
Appl. No.: 16/210,066
Filed: Dec. 5, 2018

(51) Int. Cl.
*C07F 9/6584* (2006.01)
*A61P 37/06* (2006.01)
*A61P 35/00* (2006.01)

(52) U.S. Cl.
CPC .......... *C07F 9/65846* (2013.01); *A61P 35/00* (2018.01); *A61P 37/06* (2018.01); *C07B 2200/13* (2013.01)

(58) Field of Classification Search
None
See application file for complete search history.

(56) References Cited

To view the complete listing of prior art documents cited during the proceeding for Reexamination Control Number 90/014,599, please refer to the USPTO's public Patent Application Information Retrieval (PAIR) system under the Display References tab.

*Primary Examiner* — Alan D Diamond (57) ABSTRACT

The present disclosure provides a process for preparing cyclophosphamide, intermediate, and the monohydrate thereof.

US 10,479,811 C1

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 7 and 10-12 are cancelled.

Claims 1 and 8 are determined to be patentable as amended.

Claims 2-6 and 9, dependent on an amended claim, are determined to be patentable.

1. A process for preparing cyclophosphamide monohydrate, comprising the steps of:
   (a) providing bis (2-chloroethyl) amine hydrochloride;
   (b) converting bis (2-chloroethyl) amine hydrochloride into cyclophosphamide monohydrate represented as formula I, and wherein the converting comprises the step of reacting bis (2-chloroethyl) amine hydrochloride with phosphorus oxychloride in the presence of a base in toluene at a temperature ranging from 20° C. to 60° C. to form bis-(2-chloroethyl)-phosphoramidic dichloride represented as formula II:

wherein the bis-(2-chloroethyl)-phosphoramidic dichloride represented as formula II is converted into the cyclophosphamide represented as formula I by reacting with 3-amino-1-propanol in the presence of the base in a solvent and purifying and isolating to yield a crystalline of cyclophosphamide monohydrate represented as formula I[.]; *and*

*(c) crystallizing a crystalline form A of the bis-(2-chloroethyl)-phosphoramidic dichloride represented as formula II by using a solution comprising toluene and n-heptane.*

8. The process according to claim [7] *1*, wherein the crystalline form A of the bis-(2-chloroethyl)-phosphoramidic dichloride represented as formula II is characterized by X-ray powder diffraction pattern comprising the characteristic 2θ° peaks of 13.8, 14.4, 15.4, 19.9, 23.6, 26.9, 29.0, 29.65, 31.0 and 31.9±0.2°, wherein peaks at 30.9 and 31.1±0.2° are un-split and 100% intensity peak is present at 23.6±0.2°, infrared absorption spectrum comprising the characteristic peaks approximately at 2959.5 $cm^{-1}$, 1459.3 $cm^{-1}$, 1263.3 $cm^{-1}$, 1226.3 $cm^{-1}$ and 980.3 $cm^{-1}$, and differential scanning calorimetry (DSC) exhibits melting points ranging from 56-58° C.

* * * * *